United States Patent

Boechat et al.

[11] Patent Number: 6,034,266
[45] Date of Patent: Mar. 7, 2000

[54] GEM-DIFLUORO DERIVATIVE OF PHENYLACETAMIDE AND PHENYLACETIC ACID AND THEIR PHARMACEUTICAL USES

[75] Inventors: Nubia Boechat; Angelo Da Cunha Pinto, both of Rio de Janeiro, Brazil

[73] Assignee: Fundacao Oswaldo Cruz-Fiocruz, Rio de Janeiro, Brazil

[21] Appl. No.: 08/710,399

[22] Filed: Sep. 17, 1996

Related U.S. Application Data

[63] Continuation-in-part of application No. 08/627,180, Apr. 3, 1996, abandoned.

[30] Foreign Application Priority Data

Mar. 11, 1996 [BR] Brazil ...................................... 9600975

[51] Int. Cl.$^7$ ........................ C07C 229/00; C07C 233/00
[52] U.S. Cl. ............................ 560/43; 562/444; 562/449; 564/163; 564/168; 564/169; 564/170
[58] Field of Search ............................ 560/43; 562/444, 562/449; 564/163, 168, 169, 170

[56] References Cited

U.S. PATENT DOCUMENTS 5,220,064  6/1993  Johnson .................................. 564/170

FOREIGN PATENT DOCUMENTS 2499981  8/1982  France .

OTHER PUBLICATIONS

Boechat, et al. (11th European Symposium on Fluorine Chemistry—Abstract), Sep. 1995.
Roth, H.J., et al., "Pharmaceutical Chemistry", J.Willey and Sons, vol. 1, 1988, 92–93.
Libman, J.F., et al, "Fluorine Contain Molecules", VCH Publishers, 1988.
Welch, J.T., Tetrahedron, 1987, 43,3123.
Welch, J.T., et al, "Fluorine in Broorganic Chemistry", Willey and sons, 1991.
Borthwick, A.D., et al; J.Med. Chem; 1990, 33, 179.
Boechat, et al: "Synthesis of a Series of Fluorinated Analogues of 2–Amidephenylacetic Acids", 11th European Symposium on Fluorine Chemistry, Sep. 17–22, 1995.
Koruov, A.M., et al, Tetrahedrou: Asymmetry, 1995, 6, 199.
Middleton, W.J. et al, E.M.J. Org. Chem; 1980,45,2883–2887.
Holt, J.S., et al, J. Chem. Soc., 1958, 1217.
Huntress E.H. et al; J.Am. Chem. Soc., 1949,71,745.
Maginnity, P.M., et al; J.Am. Soc. 1951,73,3579.
Programme, 11th European Symposium on Fluorine Chemistry, Bled, Slovenia, Sep. 17–22, 1995.

Primary Examiner—Paul J. Killos
Attorney, Agent, or Firm—Pillsbury Madison & Sutro

[57] ABSTRACT

The present invention refers to novel gem-difluoro compounds of formula:

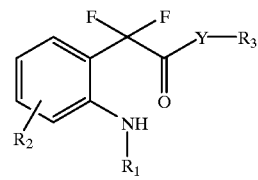

wherein: $R_1$ can be hydrogen, acyl or acyl substituted;
$R_2$ is hydrogen, lower alkyl, lower alkyl substituted, nitro, halogen, methylenedioxy, trifluoromethyl or OR';
Y is oxygen, sulfur or NR";
$R_3$ is hydrogen, lower alkyl, lower alkyl substituted, phenyl, aryl group substituted or metal selected of the group consisting of sodium, potassium, clcium, magnesium, zinc or aluminum;
R' and R" are hydrogen, lower alkyl, lower alkyl substituted, phenyl or aryl substituted; and
(a) in the group $C_1$–$C_4$ alkyl substitued, one or more the hydrogen atoms are substituted by lower alkyl, lower alkyl substituted, phenyl or aryl substituted;
(b) in the group aryl substituted, one or more of the hydrogen atoms are substituted by lower alkyl, halogen, nitro, trifluoromethyl or OR';
(c) in the group acyl substituted, one or more of the hydrogen atoms are substituted by lower alkyl, lower alkyl substituted, phenyl or aryl substituted.

The compounds as defined above are useful for the treatment of all pain disorders associated to inflammatory and/or rheumatic diseases. The present invention also provides a new process to obtain the compounds from isatin.

23 Claims, No Drawings

GEM-DIFLUORO DERIVATIVE OF PHENYLACETAMIDE AND PHENYLACETIC ACID AND THEIR PHARMACEUTICAL USES

This is a continuation-in-part (CIP) of application Ser. No. 08/627,180, filed on Apr. 3, 1996, which was abandoned upon the filing hereof.

The present invention relates to new fluorinated phenylacetic and phenylacetamide derivatives and its uses as non-steroidal antiinflammatory and antirheumatic agents, having analgesic and antipyretic activities which are useful for the treatment of all pain disorders associated to inflammatory and/or rheumatic diseases.

BACKGROUND OF THE INVENTION

It is well known that many compounds of general formula (I) having a phenylacetic acid skeleton present biological activity as antiinflammatory and antirheumatic agents. Besides the antiinflammatory effect most of the compounds in this class have also analgesic and antipyretic activities. Some examples of such substances are diclofenac, flurbiprofen and ibuprofen (Roth, H. J. and Kleemann, A., "Pharmaceutical Chemistry", Vol. 1, Pp. 92–93, John Wiley and Sons, Chichester, 1988).

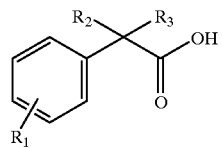

(I)

U.S. Pat. No. 5,220,064 describes substituted 4'-hydroxy phenylacetic acid and phenylacetamide derivatives having antiinflammatory and analgesic activities. Among the compounds included in the definition of formula I of the patent there are the following:

wherein $R_2$ could be hydrogen or lower alkyl, B could be

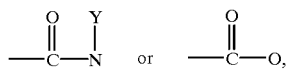

but X must be hydrogen or lower alkyl, i.e. X can not be halogen. Moreover, X is never a gem-difluoro group. Also the aromatic ring always has hydroxyl group at para position.

FR 2,499,981 describes a synthesis of phenylacetic acid derivative obtained by basic hydrolysis of 7-benzoyl-methylindol-2-one with general formula as followed:

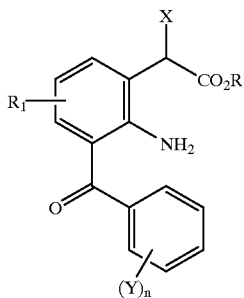

Wherein $R_1$ is always methyl and X is hydrogen, never a gem-difluoro group.

Important differences in biological activity may commonly be expected based on the difference in eletronegativity between fluorine and hydrogen as well as the higher C—F bond strength versus the strength of the C—H bond. In addition, as a consequence of the electron density, fluorine can function as hydrogen bond acceptor at the active site (Libman, J. F; Greenberg, A. and Dolbier Jr., W. R. "Fluorine Contain Molecules", VCH Publishers, New York, 1988). Indeed, a great variety of biologically active compounds having the so-called gem-difluoro function ($CF_2$), such as sugars, nucleic acids, prostaglandins, steroids, are known and have been described in: (i) Welch, J. T. Tetrahedron, 1987, 43, 3123; (ii) Welch, J. T. and Eswarakrishan, S., "Fluorine in Bioorganic Chemistry", J. Wiley & Sons., N. York, 1991. (iii) Borthwick, A. D. et al, J. Med. Chem., 1990, 33, 179; (iv) Kornov, A. M. et al, Tetrahedron: Asymmetry, 1995, 6, 199.

Some α,α-difluorophenylacetic acids and α,α-difluorophenylacetamide derivatives were prepared by the selective replacement of the α-oxo group from α-oxoarylacetates using DAST (diethylamino sulfur trifluoride) as fluorinating reagent (Middleton, W. J. and Bingham, E. M., J. Org. Chem., 1980, 45, 2883–2887). According to Middleton and Bingham, it could be expected some change on the biological activity when two fluorine atoms are introduced in α,α-difluoroarylacetic acid compounds. However, the type and/or intensity of the possible modifications are unpredictable as demonstrated by the examples presented. The difluoro analogue (α,α-difluoro-4-isobutyl-phenylacetic acid) of the synthetic antiinflammatory drug ibufenac (4-isobutyl-phenylacetic acid) prepared by the authors was essentially inactive as an antiinflammatory agent, while the difluoro analogue (α,α-difluoro-α-naphthylacetic acid) of the plant-growth regulate (α-naphthylacetic acid) had a comparable biological activity.

Isatins (indol-2,3-diones) of general formula (II) are versatile starting materials for a variety of other important classes of heterocyclic compounds. They can be easily prepared from inexpensive and available anilines (Holt, J. S. et al,J. Chem. Soc., 1958, 1217; Huntress, E. H. et al,J. Am. Chem. Soc., 1949, 71, 745; Maginnity, P. M. et al, J. Am. Chem. Soc., 1951, 73, 3579). Isatins have two different carbonyl groups, the C-3 carbonyl having a strong ketonic character and, thus suitable to react selectively with DAST (diethylamino sulfur trifluoride), a specific reagent for nucleophilic addition to ketone and aldehyde carbonyls, to give gem-difluoroindoles.

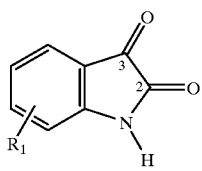

(II)

To overcome the difficulties in producing synthetic anti-inflammatory and antirheumatic agents with high yields and high biological activities, the present invention provides a process to synthesise novel gem-difluoro derivatives of phenylacetic acid and phenylacetamide from of the fluorination of isatins with DAST and subsequently reaction with alcohols, thiols, water, hydroxides solutions and amines, with concomitant opening of heterocyclic ring.

SUMMARY OF THE INVENTION

The present invention relates to novel compounds of a formula:

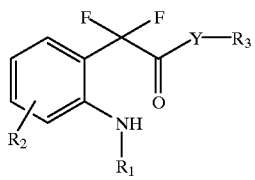

(IV)

wherein: $R_1$ can be hydrogen, acyl or acyl substituted;

$R_2$ is hydrogen, lower alkyl, lower alkyl substituted, nitro, halogen, methylenedioxy, trifluoromethyl or OR';

Y is oxygen, sulfur or NR";

$R_3$ is hydrogen, lower alkyl, lower alkyl substituted, phenyl, aryl group substituted or metal selected of the group consisting of sodium, potassium, clcium, magnesium, zinc or aluminum;

R' and R" are hydrogen, lower alkyl, lower alkyl substituted, phenyl or aryl substituted.

The terms herein employed have the following meanings:

"lower alkyl" means a straight or branched hydrocarbon chain of from one to four carbon atoms;

"lower alkyl substituted" means the substitution of one or more of the hydrogen atoms by lower alkyl, lower alkyl substituted, phenyl or aryl substituted;

"aryl substituted" means the substitution of one or more of the hydrogen atoms by lower alkyl, halogen, nitro, trifluoromethyl or OR';

"halogen" means fluoro, chloro or bromo;

"acyl substituted" means the substitution of one or more of the hydrogen atoms by lower alkyl, lower alkyl substituted, phenyl or aryl substituted.

According to the present invention, compounds of formula IV are prepared in two steps: the first is the reaction of an isatin with DAST and, the second is (i) a solvolysis of the product of the first step, the gem-difluoroxindol derivative (III), with water, metalic hydroxides, alcohols or thiols, or (ii) reaction with amines. The metalic hydroxides can have the cation used in pharmaceutical compounds (sodium, potassium, calcium, magnesium, zinc or aluminium). These reaction steps can be represented as follows:

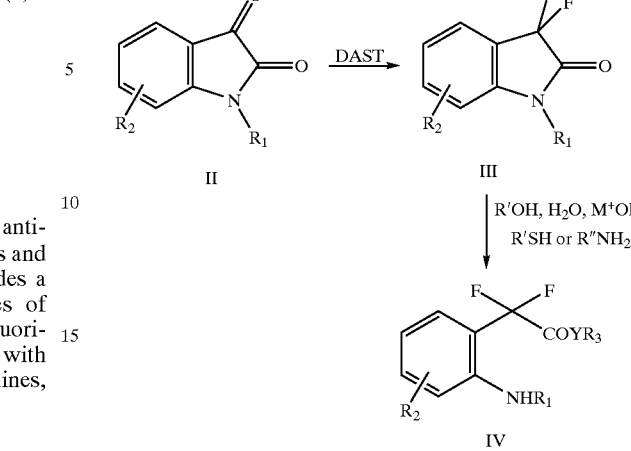

DETAILED DESCRIPTION OF THE INVENTION

The selective fluorination of isatins followed by the opening of the heterocyclic ring is a new and interesting approach to prepare important pharmaceutical compounds α,α-difluorophenylacetic acid derivatives and α,α-difluorophenylacetamide derivatives.

The reaction of isatin or substituted isatins with DAST is carried out by contacting directly the reagents at 60° C. in the absence of solvent or, at room temperature in the presence of solvents such as $CH_2Cl_2$ or $CCl_4$. The product is the correspondent indol compound.

Isatins used in the present invention have different groups attached at heterocyclic atom and/or at the aromatic ring.

In the present invention, it was found that the nucleophilicity of C-2 of indol compounds is enhanced by the presence of the gem-difluoro group, aiding the further reaction of the indol compound with either weak and strong nucleophilic reagents with simultaneous opening of the heterocyclic ring. Indeed, 1-acetyl-2-oxo-3,3-difluoro-indol is highly reactive with nucleophilic solvents and, moreover, it reacts easily with amines producing gem-difluoro-phenylacetamide derivatives.

The following examples are illustrative of the invention and represent preferred bodiments. Other modifications may be readily produced by suitable variations of reactions and of the substituent groups in the compounds.

Example 1

Fluorination of Isatins with DAST:

To a 100 ml two neck round bottom flask containing 6,3 mmoles of isatin (or substituted isatins) dissolved in 15 ml of dichloromethane, were added 3,4 ml (25,3 mmoles) of DAST. The mixture was magnetically stirred at room temperature during 6 hours. The solution was cooled and 5 ml of cold water were dropwise introduced into the flask. The organic phase was separated and washed twice with 5 ml of cold water. The organic phase consisting on dichloromethane solution was dried under sodium sulfate and evaporated. Some of obtained difluoro derivatives are presented in table below:

TABLE 1 examples of 3,3-difluor-2-oxoindols obtained from isatin with DAST

| # | Compound | $^{19}$F-NMR CDCl$_3$ (δ) | Melting Point (° C.) | Yield (%) |
|---|---|---|---|---|
| 1 | 3,3-difluoro-2-oxindol | −112,76 | 137–139 | 85 |
| 2 | 1-acetyl-3,3-difluoro-2-oxindol | −106,45 | 109–111 | 94 |
| 3 | 1-acetyl-3,3-difluoro-5-methyl-2-oxindol | −106,20 | 72–74 | 93 |
| 4 | 1-benzoyl-3,3-difluoro-2-oxindol | −106,68 | 138–139 | 95 |
| 5 | 1-chloroacetyl-3,3-difluoro-2-oxindol | −105,83[a] | 113–115 | 86 |
| 6 | 5-chloro-3,3-difluoro-2-oxindol | −112,37 | 183–185 | 90 |
| 7 | 3,3-difluoro-2-oxo-7-trifluoro-methylindol | −112,50[a] −61,32 | 138–139 | 76 |
| 8 | 3,3-difluoro-5-nitro-2-oxindol | −111,45[b] | 179–181 | 67 |
| 9 | 1-choroacetyl-3,3-difluoro-5-methyl-2-oxindol | 105,77 | oil | 70 |
| 10 | 2-(N-acetamide)-3,3-difluoro-2-oxo-4-trifluoromethylindol | −106,25[b] −61,39 | oil | 70 |
| 11 | 3,3-difluoro-7-methyl-2-oxindol | −111,02 | 128–140 | 78 |

Notes:
[a] (CD$_3$)$_2$CO;
[b] DMSO$_{d6}$

Example 2

Synthesis of the gem-difluorophenylacetic acid, salt and ester derivatives

The difluoro-2-oxoindol obtained in the precedent examples was dissolved in a suitable nucleophylic solution, e.g anhydrous alcohol or thiol or acetone/water or water hydroxide solution and the mixture was stirred at room temperature for 24 hours. The correspondent ester, thioester, acid or metalic salt was obtained, respectively.

TABLE 2

2-(N-acetamide)-α,α-difluorophenylacetic acid and ester prepared by the method of the present invention

| # | Compound | $^{19}$F-NMR CDCl$_3$ (δ) | Melting Point (° C.) | Yield (%) |
|---|---|---|---|---|
| 12 | 2-(N-acetamide-α,α-difluoro-phenylacetic acid | −102,54[a] | 170–172 | 100 |
| 13 | methyl 2-(N-acetamide)-α,α-difluoro-phenylacetate | −103,37 | 112–116 | 92 |
| 14 | methyl 2-(N-acetamide)-α,α-difluoro-5-methyl-phenylacetate | −103,22 | 101–103 | 90 |
| 15 | methyl 2-(N-benzamide)-α,α-difluoro-phenylacetate | −103,59 | 118–120 | 83 |
| 16 | 2-(N-chloroacetamide)-α,α-difluoro-phenylacetic acid | −102,11[b] | 123–125 | 94 |
| 17 | methyl 2-(N-chloroacetamide)-α,α-difluorophenylacetate | −103,39[b] | oil | 76 |

Notes:
[a] plus DMSO$_{36}$
[b] (CD$_3$)$_2$CO

Example 3

Synthesis of the gem-difluorophenylacetamide Derivatives

To a 100 ml two neck round bottom flask was introduced 1 g (4,7 mmol) of Acyl-difluoroxindole, 20 ml of dichloromethane and 47 mmoles of the suitable substituted amine. The mixture was stirred at the room temperature for 2 hours, the organic phase was extracted three times with 10 ml of HCl 0,6N followed by a washing step with 10 ml of water for three times. The product was dried under sodium sulfate and the solvent evaporated resulting in the corresponding α,α difluorophenylacetamide compound.

TABLE 3

2-(N-acetamide)-α,α-difluorophenylacetamide prepared by the method of the present invention

| # | Compound | $^{19}$F-NMR CDCl$_3$ (δ) | Melting Point (° C.) | Yield (%) |
|---|---|---|---|---|
| 18 | isopropyl 2-(N-acetamide-α,α-difluorophenylacetamide | −104,23[a] | 115–118 | 80 |
| 19 | 4'-chlorophenyl 2-(N-acetamide)-α,α-difluorophenylacetamide | −102,08 | 172–173 | 55 |
| 20 | phenyl 2-(N-acetamide)-α,α-difluorophenylacetamide | −102,16 | 168–170 | 81 |
| 21 | benzyl 2-(N-acetamide)-α,α-difluorophenylacetamide | −100,81 | 149–151 | 64 |
| 22 | benzyl 2-(N-benzamide)-α,α-difluorophenylacetamide | −102,09 | 151–153 | 71 |

Examples of antiinflammatory and antirheumatic agents with analgesic and antipyretic activities of the present invention include, among others, the compounds of Table 4.

TABLE 4
Examples of Particularly Valuable Compounds Are the Following:
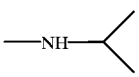
| YR₃ | R₁ | R₂ | Compound Designation |
|---|---|---|---|
|  | | H | (1) |
| | —COCH₃ | 5-Me | (2) |
| | | 3-Me | (3) |
| | | 5-NO₂ | (4) |
| | | 5-Cl | (5) |
| | | 6-CF₃ | (6) |
| | —COCH₂Cl | H | (7) |
| |  | H | (8) |
| | 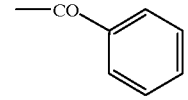 | H | (9) |
| | 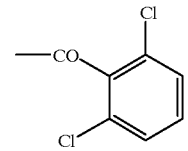 | H | (10) |
| | 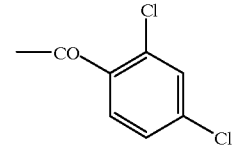 | H | (11) |
| 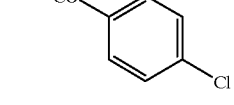 | —COCH₃ | H | (12) |
| 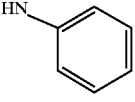 | —COCH₃ | H | (13) |
|  | —COCH₃ | H | (14) |

TABLE 4-continued

Examples of Particularly Valuable Compounds Are the Following:

[Structure: benzene ring with CF$_2$-COYR$_3$ group, NH-R$_1$ group, and R$_2$ substituent]

| YR$_3$ | R$_1$ | R$_2$ | Compound Designation |
|---|---|---|---|
| HN-CH$_2$-C$_6$H$_5$ (benzylamine) | —CO—O—C$_6$H$_5$ (phenoxycarbonyl) | H | (15) |
| OH | —COCH$_3$ | H | (16) |
|  |  | 5-Cl | (17) |
|  |  | 5-NO$_2$ | (18) |
|  |  | 6-CF$_3$ | (19) |
|  |  | 3-Me | (20) |
|  | —COCH$_2$Cl | H | (21) |
|  |  | 5-Cl | (22) |
|  |  | 5-NO$_2$ | (23) |
|  |  | 3-Me | (24) |
|  |  | 6-CF$_3$ | (25) |
|  | —CO—O—C$_6$H$_5$ | H | (26) |
|  |  | 3-Me | (27) |
|  |  | 5-Cl | 28 |
|  | —CO—O—C$_6$H$_4$-Cl (4-chlorophenoxycarbonyl) | H | (29) |
|  |  | 5-NO$_2$ | (30) |
|  |  | 6-CF$_3$ | (31) |
|  |  | 3-Me | (32) |
|  | —CO—O—(2,6-dichlorophenyl) | H | (33) |
|  |  | 5-Cl | (34) |
|  |  | 5-NO$_2$ | (35) |
|  |  | CF$_3$ | (36) |
| OH | —CO—O—(2,4-dichlorophenyl) | H | (37) |
| O$^-$ M$^+$ | H | H | (38) |
|  |  | 5-NO$_2$ | (39) |
|  |  | 6-CF$_3$ | (40) |
|  |  | 5-Cl | (41) |
|  |  | 5-Me | (42) |
|  |  | 3-Me | (43) |
|  |  | 3,5-diBr | (44) |
| OR' | —COCH$_3$ | H | (45) |
|  |  | 5-NO$_2$ | (46) |
|  |  | 6-CF$_3$ | (47) |
|  |  | 5-Cl | (48) |
|  |  | 5-Me | (49) |
|  |  | 3-Me | (50) |
|  |  | 3,5-diBr | (51) |

Notes:
M$^+$= Na; K; Ca; Mg; Zn and Al.
R'= hydrogen, C$_1$–C$_4$ alkyl, C$_1$–C$_4$ alkyl substituted, phenyl or aryl substituted.

Some examples of preferred compounds are named in Table 5 below.

TABLE 5

Some preferred compounds included in general formula IV of the present invention:

| Comp. n° | Compound Name |
|---|---|
| (1) | N-isopropyl-α,α-difluoro-2-(N-acetamide)-phenylacetamide |
| (2) | N-isopropyl-α,α-difluoro-2-(N-acetamide)-5-methylphenylacetamide |
| (3) | N-isopropyl-α,α-difluoro-2-(N-acetamide)-3-methylphenylacetamide |
| (4) | N-isopropyl-α,α-difluoro-2-(N-acetamide)-5-nitro-phenylactamide |
| (5) | N-isopropyl-α,α-difluoro-2-(N-acetamide)-5-chloro-phenylacetamide |
| (6) | N-isopropyl-α,α-difluoro-2-(N-acetamide)-3,5-dibromophenylacetamide |
| (7) | N-isopropyl-α,α-difluoro-2-(N-acetamide)-6-trifluoromethylphenylacetamide |
| (8) | N-isopropyl-α,α-difluoro-2-(N-acetamide)-3-trifluoromethylphenylacetamide |
| (9) | N-isopropyl-α,α-difluoro-2-(N-acetamide)-4,5-methylenedioxiphenylacetamide |
| (10) | N-isopropyl-α,α-difluoro-2-(N-chloroacetamide)-phenylacetamide |
| (11) | N-isopropyl-α,α-difluoro-2-(N-benzoyl)-phenylacetamide |
| (12) | N-isopropyl-α,α-difluoro-2-(N-4'-chlorobenzoyl)-phenylacetamide |
| (13) | N-isopropyl-α,α-difluoro-2-(N-2',4'-dichlorobenzoyl)-phenylacetamide |
| (14) | N-isopropyl-α,α-difluoro-2-(N-2',6'-dichlorobenzoyl)-phenylacetamide |
| (15) | N-isopropyl-α,α-difluoro-2-(N-benzoyl)-5-methylphenylacetamide |
| (16) | N-isopropyl-α,α-difluoro-2-(N-benzoyl)-5-nitrophenylacetamide |
| (17) | N-isopropyl-α,α-difluoro-2-(N-4'-chlorobenzoyl)-5-methylphenylacetamide |
| (18) | N-isopropyl-α,α-difluoro-2-(N-2',4'-dichlorobenzoyl)-5-methylphenylacetamide |
| (19) | N-isopropyl-α,α-difluoro-2-(N-2',6'-dichlorobenzoyl)-5-methylphenylacetamide |
| (20) | N-phenyl-α,α-difluoro-2-(N-acetamide)-phenylacetamide |
| (21) | N-phenyl-α,α-difluoro-2-(N-acetamide)-5-methylphenylacetamide |
| (22) | N-phenyl-α,α-difluoro-2-(N-acetamide)-6-trifluoromethylphenylacetamide |
| (23) | N-phenyl-α,α-difluoro-2-(N-2',6'-dichlorobenzoyl)-phenylacetamide |
| (24) | N-phenyl-α,α-difluoro-2-(N-4'-chlorobenzoyl)-phenylacetamide |
| (25) | N-phenyl-α,α-difluoro-2-(N-acetamide)-3,5-dibromophenylacetamide |
| (26) | N-(4'-chlorophenyl)-α,α-difluoro-2-(N-acetamide)-phenylacetamide |
| (27) | N-(4'-chlorophenyl)-α,α-difluoro-2-(N-acetamide)-5methylphenylacetamide |
| (28) | N-(4'-chlorophenyl)-α,α-difluoro-2-(N-acetamide)-6-nitrophenylacetamide |
| (29) | N-(4'-chlorophenyl)-α,α-difluoro-2-(N-chloroacetamide)-phenylacetamide |
| (30) | N-(2,4-difluorophenyl)-α,α-difluoro-2-(N-acetamide)-phenylacetamide |
| (31) | N-(2,4-difluorophenyl)-α,α-difluoro-2-(N-acetamide)-5-methylphenylacetamide |
| (32) | N-(2,4-difluorophenyl)-α,α-difluoro-2-(N-acetamide)-3-trifluoromethyl-phenylacetamide |
| (33) | N-(2,4-difluorophenyl)-α,α-difluoro-2-(N-benzoyl)-phenylacetamide |
| (34) | N-benzyl-α,α-difluoro-2-(N-benzoyl)-phenylacetamide |
| (35) | N-benzyl-α,α-difluoro-2-(N-acetamide)-phenylacetamide |
| (36) | N-benzyl-α,α-difluoro-2-(N-acetamide)-5-nitrophenylacetamide |
| (37) | N-benzyl-α,α-difluoro-2-(N-2',6'-dichlorobenzoyl)-phenylacetamide |
| (38) | α,α-difluoro-2-(N-acetamide)-phenylacetic acid |
| (39) | α,α-difluoro-2-(N-acetamide)-3-methylphenylacteic acid |
| (40) | α,α-difluoro-2-(N-acetamide)-5-chlorophenylacetic acid |
| (41) | α,α-difluoro-2-(N-acetamide)-nitrophenylacetic acid |
| (42) | α,α-difluoro-2-(N-acetamide)-6-trifluoromethylphenylacetic acid |
| (43) | α,α-difluoro-2-(N-chloroacetamide)-3-methylphenylacetic acid |
| (44) | α,α-difluoro-2-(N-chloroacetamide)-5-chlorophenylacetic acid |
| (45) | α,α-difluoro-2-(N-chloroacetamide)-nitrophenylacetic acid |
| (46) | α,α-difluoro-2-(N-chloroacetamide)-3,5-dibromophenylacetic acid |
| (47) | α,α-difluoro-2-(N-benzoyl)-5-nitrophenylacetic acid |
| (48) | α,α-difluoro-2-(N-benzoyl)-5-chlorophenylacetic acid |
| (49) | α,α-difluoro-2-(N-benzoyl)-3-methylphenylacetic acid |
| (50) | α,α-difluoro-2-(N-benzoyl)-6-trifluoromethyphenylacetic acid |
| (51) | α,α-difluoro-2-(N-2',4'-dichlorobenzoyl)-phenylacetic acid |
| (52) | α,α-difluoro-2-(N-2',6'-dichlorobenzoyl)-5-methylphenylacetate |
| (53) | α,α-difluoro-2-(N-4'-chlorobenzoyl)-phenylacetic acid |
| (54) | α,α-difluoro-2-(N-4'-chlorobenzoyl)-5-nitrophenylacetic acid |
| (55) | methyl α,α-difluoro-2-(N-acetamide)-phenylacetate |
| (56) | methyl α,α-difluoro-2-(N-acetamide)-5-methylphenylacetate |
| (58) | methyl α,α-difluoro-2-(N-acetamide)-5-nitrophenylacetic acid |
| (59) | methyl α,α-difluoro-2-(benzoyl)-phenylacetate |
| (60) | methyl α,α-difluoro-2-(N-4'-chlorobenzoyl))-phenylacetate |
| (61) | methyl α,α-difluoro-2-(N-2',4'-dichlorobenzoyl)-phenylacetate |
| (62) | methyl α,α-difluoro-2-(N-2',6'-dichlorobenzoyl)-phenylacetate |
| (63) | ethyl α,α-difluoro-2-(N-acetamide)-phenylacetate |
| (64) | ethyl α,α-difluoro-2-(N-4'-chlorobenzoyl)-phenylacetate |
| (65) | ethyl α,α-difluoro-2-(N-2',4'-dichlorobenzoyl)-phenylacetate |
| (66) | isopropyl α,α-difluoro-2-(N-2',6'-dichlorobenzoyl)-phenylacetate |
| (67) | Isopropyl α,α-difluoro-2-(N-acetamide)-phenylacetate |
| (68) | Isopropyl α,α-difluoro-2-(N-4'-chlorobenzoyl)-phenylacetate |
| (69) | Isopropyl α,α-difluoro-2-(N-2',4'-dichlorobenzoyl)-phenylacetate |

TABLE 5-continued

Some preferred compounds included in general formula IV of the present invention:

| Comp. n° | Compound Name |
|---|---|
| (71) | nbuthyl α,α-difluoro-2-(N-acetamide)-phenylacetate |
| (72) | nbuthyl α,α-difluoro-2-(N-4'-chlorobenzoyl)-phenylacetate |
| (73) | nbuthyl α,α-difluoro-2-(N-2',4'-dichlorobenzoyl)-phenylacetate |
| (74) | nbuthyl α,α-difluoro-2-(N-2',6'-dichlorobenzoyl)-phenylacetate |
| (75) | sodium αl,α-difluoro-2-amino-3-methyl-phenylacetate |
| (76) | sodium αl,α-difluoro-2-amino-phenylacetate |
| (77) | sodium αl,α-difluoro-2-amino-5-methyl-phenylacetate |
| (78) | potassium αl,α-difluoro-2-amino-5-nitro-phenylacetate |
| (79) | potassium αl,α-difluoro-2-amino-5-chloro-phenylacetate |
| (80) | potassium αl,α-difluoro-2-amino-6-trifluoromethyl-phenylacetate |

Example 4

Antinflammatory Assay (cell migration and protein extravasation):

Forty four male Swiss mice (20–30 g), from our own colony, were lodged in a room with controlled temperature (23±2° C.) and lighting (lights on from 7:00 to 19:00 h), with free access to lab chow and tap water.

Induction of Pleurisy

Non-fasted male mice (20–25 g) were treated orally with 50–200 mg/kg of the compounds, 1 hour before the inflammatory stimullus. Pleurisy was induced by the tecnique of Spector (1956), modified for mice as teached by Henriques et al., (1990). Briefly, an adapted needle (13×5 gauge) was carefully inserted 2 mm through the parietal pleura into the right side of the thoracic cavity, under light ether anaesthesia, to enable a 50 μl injection of either carrageenan (300 mg cavity$^{-1}$) or sterile saline in control groups.

The animals were killed 4 h after injection carrageenan. Their thoracic cavities were washed with 1 ml of PBS containing heparin (20 iu ml$^{-1}$) and the fluid lavage collected for assessement of leukocyte accumulation and Evans blue extravasation.

Leucocyte Counts

The pleural lavage fluid collected was diluted 40 times in Turk's solution and total leukocyte counts were made in Neubauer chambers under light microscopy. Differential leukocyte counts were determined in cytocentrifuged smears stained with May-Grünwald-Giemsa dye using an oil immersion objective (100×).

Protein Extravasation

For these experiments, mice were given an intravenous injection of Evans blue (25 mg kg$^{-1}$) 24 h before the inflammatory stimulus. The pleural lavage fluid was collected at the same times and as described above, centrifuged (2,500 rpm for 10 min) and the absorbance of the cell free supernatant was read in a spectrophotometer (Schimadzu, Japan) at 600 nm.

Statistical Analysis

Results are presented as means ±s.d.means and were statistically evaluated by analysis of variance followed by the Newman-Keuls-student t-test. The significance level was set at P≦0.05.

Results:

Total leukocyte were inhibited from 3.44±0.14×10$^6$ (carrageenan injected group) to 1.68±0.17×10$^6$ (compound: N-Isopropyl α,α-difluoro-2-(N-acetamide)-phenylacetamide (MG06)), 2.3±0.56 (compound: N-Phenyl α,α-difluoro-2-(N-acetamide)-phenylacetamide (MG07)), 2.43±0.35 (compound: N-4' phnenyl α,α-difluoro-2-(N-acetamide)-phenylacetamide (MG08)).

Neutrophils were inhibited from 1.93±0.46×10$^6$ (carrageenan group) to 0.28±0.03×10$^6$ (MG06), 0.57±0.12× 10$^6$ (MG07), 0.49±0.18×10$^6$ (MG08).

Pre-treatment with MG06, MG07 or MG08 inhibited in 63%, 43% 45% respectively, the protein extravasation induced by intra-thoracic injection of carrageenan.

We claim:

1. A compound having a formula:

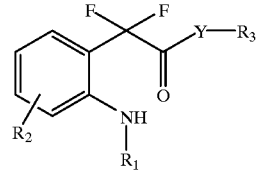

wherein: $R_1$ is hydrogen, acyl or acyl substituted;

$R_2$ is hydrogen, lower alkyl, lower alkyl substituted, nitro, halogen, methylenedioxy, trifluoromethyl or OR';

Y is oxygen, sulfur or NR";

$R_3$ is hydrogen, lower alkyl, lower alkyl substituted, aryl group substituted or unsubstituted, or metal selected of the group consisting of sodium, potassium, calcium, magnesium, zinc or aluminum;

R' and R" are hydrogen, lower alkyl, lower alkyl substituted, or aryl substituted or unsubstituted; and (a) in the group $C_1$–$C_4$ alkyl substituted, one or more the hydrogen atoms are substituted by lower alkyl, lower alkyl substituted, or aryl substituted or unsubstituted;

(b) in the group aryl substituted, one or more of the hydrogen atoms are substituted by lower alkyl, halogen, nitro, trifluoromethyl or OR';

(c) in the group acyl substituted, one or more of the hydrogen atoms are substituted by lower alkyl, lower alkyl substituted, or aryl substituted or unsubstituted.

2. A compound according to claim 1 wherein Y is NR", $R_1$ is acyl, acyl substituted and $R_2$ is hydrogen, methyl, nitro, trifluoromethyl, methylenedioxy, fluoro, chloro, bromo or OR'.

3. A compound according to claim 1 wherein Y is oxygen and $R_3$ is hydrogen with the provisos that $R_1$ must be acyl or acyl substituted and $R_2$ can not be 5-methyl.

4. A compound according to claim 1 wherein Y is oxygen with the provisos that $R_1$ is acyl substituted and $R_2$ is hydrogen, methyl, nitro, trifluoromethyl, methylenedioxy, fluoro, chloro or bromo and $R_3$ is not a metal and not hydrogen.

5. A compound according to claim 1 wherein Y is oxygen and $R_3$ is a metal selected from the group consisting of sodium, potassium, calcium, magnesium, zinc or aluminum with the provisos that $R_1$ must be hydrogen and $R_2$ is hydrogen, methyl, nitro, trifluoromethyl, methylenedioxy, fluoro, chloro or bromo.

6. A compound according to claim 2 wherein $R_1$ is acetyl, $R_2$ is hydrogen and R" is hydrogen and $R_3$ is isopropyl.

7. A compound according to claim 3 wherein $R_1$ is acetyl and $R_2$ is hydrogen.

8. A compound according to claim 4 wherein $R_3$ is acetyl, $R_2$ is 5-Mehtyl and R' is methyl.

9. A compound according to claim 5 wherein $R_2$ is 3-Methyl and $R_3$ is sodium.

10. A process for producing a compound of formula:

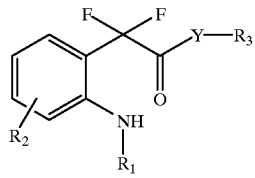

wherein $R_1$, $R_2$, $R_3$ and Y are as defined in claim 1, which process comprises the steps:
(a) reacting indol-2,3-dione or indol-2,3-dione having $R_1$ and $R_2$ as substituents with diethylamino sulfur trifluoride to obtain the correspondent gem-difluoroxindol; and
(b) reacting the product of step (a) with a suitable nucleophilic reagent to open the heterocyclic ring to obtain the correspondent gem-difluoro derivative of phenylacetic acid, its esters, salts and phenylacetamide.

11. A process according to claim 10 wherein the step (a) is carried out at 60° C. in the absence of solvent.

12. A process according to claim 10 wherein the step (a) is carried out at room temperature in the presence of a suitable solvent.

13. A process according to claim 12 wherein the suitable solvent is dichloromethane or tetrachloromethane.

14. A pharmaceutical composition comprising a compound according to claim 1 as an active ingredient in admixture or otherwise associated with a pharmaceutically acceptable diluent or carrier.

15. A pharmaceutical composition according to claim 14 wherein the active ingredient is N-Isopropyl α,α-difluoro-2-(N-acetamide)-phenylacetamide.

16. A pharmaceutical composition according to claim 14 wherein the active ingredient is α,α-difluoro-2-(N-acetamide)-phenylacetic acid.

17. A pharmaceutical composition according to claim 14 wherein the active ingredient is Methyl α,α-difluoro-2-(N-acetamide)-5-Methyl-phenylacetate.

18. A pharmaceutical composition according to claim 14 wherein the active ingredient is Sodium α,α-difluoro-2-amino-3-Methyl-phenylacetate.

19. A process according to claim 10 wherein the nucleophilic reagent is an anhydrous alcohol, thiol, a mixture of acetone and water or an aqueous hydroxide solution to produce a compound having the following formula:

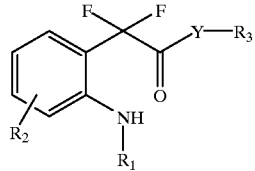

wherein: $R_1$ is hydrogen, acyl or acyl substituted;

$R_2$ is hydrogen, lower alkyl, lower alkyl substituted, nitro, halogen, methylenedioxy, trifluoromethyl or OR' with the proviso that $R_2$ is not 5-methyl;

Y is oxygen or sulfur;

$R_3$ is hydrogen, lower alkyl, lower alkyl substituted, aryl group substituted or unsubstituted, or metal selected from the group consisting of sodium, potassium, calcium, magnesium, zinc or aluminum;

R' is hydrogen, lower alkyl, lower alkyl substituted, or aryl substituted or unsubstituted; and
(a) in the group $C_1$–$C_4$ alkyl substituted, one or more the hydrogen atoms are substituted by lower alkyl, lower alkyl substituted, or aryl substituted or unsubstituted;
(b) in the group aryl substituted, one or more of the hydrogen atoms are substituted by lower alkyl, halogen, nitro, trifluoromethyl or OR';
(c) in the group acyl substituted, one or more of the hydrogen atoms are substituted by lower alkyl, lower alkyl substituted, or aryl substituted or unsubstituted.

20. The process according to claim 19 wherein Y is oxygen and $R_3$ is hydrogen.

21. The process according to claim 19 wherein Y is oxygen and $R_3$ is a metal selected from the group consisting of sodium, potassium, calcium, magnesium, zinc or aluminum.

22. A process according to claim 10 wherein the nucleophilic reagent is an amine optionally substituted to produce a compound having the following formula:

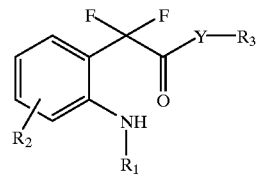

wherein: $R_1$ is hydrogen, acyl or acyl substituted;

$R_2$ is hydrogen, lower alkyl, lower alkyl substituted, nitro, halogen, trifluoromethyl, methylenedioxy or OR';

Y is NR";

$R_3$ is hydrogen, lower alkyl, lower alkyl substituted, or aryl group substituted or unsubstituted;

R' and R" are hydrogen, lower alkyl, lower alkyl substituted, or aryl substituted or unsubstituted; and
(a) in the group $C_1$–$C_4$ alkyl substituted, one or more the hydrogen atoms are substituted by lower alkyl, lower alkyl substituted, or aryl substituted or unsubstituted;
(b) in the group aryl substituted, one or more of the hydrogen atoms are substituted by lower alkyl, halogen, nitro, trifluoromethyl or OR';
(c) in the group acyl substituted, one or more of the hydrogen atoms are substituted by lower alkyl, lower alkyl substituted, or aryl substituted or unsubstituted.

23. The process according to claim 19 wherein Y is oxygen and $R_3$ is lower alkyl, lower alkyl substituted, or aryl group substituted or unsubstituted.

* * * * *